(12) United States Patent
Himes et al.

(10) Patent No.: US 11,298,500 B2
(45) Date of Patent: Apr. 12, 2022

(54) VALVE ARRANGEMENT FOR FULL FACE MASK

(71) Applicant: KONINKLIJKE PHILIPS N.V., Eindhoven (NL)

(72) Inventors: Kevin Daniel Himes, Irwin, PA (US); Derrick Blake Andrews, Markleton, PA (US); Robert Earl Hieber, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 16/498,560

(22) PCT Filed: Mar. 20, 2018

(86) PCT No.: PCT/EP2018/056918
§ 371 (c)(1),
(2) Date: Sep. 27, 2019

(87) PCT Pub. No.: WO2018/177794
PCT Pub. Date: Oct. 4, 2018

(65) Prior Publication Data
US 2020/0046933 A1  Feb. 13, 2020

Related U.S. Application Data

(60) Provisional application No. 62/477,608, filed on Mar. 28, 2017.

(51) Int. Cl.
*A61M 16/20* (2006.01)
*A61M 16/06* (2006.01)
(Continued)

(52) U.S. Cl.
CPC ...... *A61M 16/208* (2013.01); *A61M 16/0683* (2013.01); *F16K 15/16* (2013.01); *F16K 27/0209* (2013.01)

(58) Field of Classification Search
CPC ........ A61M 16/20; A61M 16/207–209; A61M 16/0683; A61M 2202/0225;
(Continued)

(56) References Cited

U.S. PATENT DOCUMENTS

| | | | |
|---|---|---|---|
| 5,647,355 A * | 7/1997 | Starr | A61M 16/208 128/205.24 |
| 8,646,449 B2 | 2/2014 | Bowsher | |

(Continued)

FOREIGN PATENT DOCUMENTS

EP   2601994 A2   6/2013

*Primary Examiner* — Elliot S Ruddie
(74) *Attorney, Agent, or Firm* — Michael W. Haas (57) ABSTRACT

A valve arrangement (60) is for a patient interface device (10) having a frame portion (16). The valve arrangement includes a valve member (36) having a coupling portion (44) and a blocking portion (46) extending from the coupling portion. The coupling portion of the valve member is structured to be coupled to the frame portion. The blocking portion is structured to move between a first position and a second position. The valve arrangement further includes a guard member (40) having a coupling portion (48) and a protecting portion (50) extending from the coupling portion of the guard member. The coupling portion of the guard member is structured to be coupled to the frame portion. When the blocking portion of the valve member moves from the first position toward the second position, the blocking portion moves toward the protecting portion of the guard member.

7 Claims, 8 Drawing Sheets

(51) Int. Cl.
*F16K 15/16* (2006.01)
*F16K 27/02* (2006.01)

(58) Field of Classification Search
CPC .......... A61M 16/0816; A61M 16/0875; A61M 16/06; F16K 15/14; F16K 15/16; F16K 27/0209
See application file for complete search history.

(56) References Cited

U.S. PATENT DOCUMENTS

| | | |
|---|---|---|
| 9,220,860 B2 | 12/2015 | Davidson |
| 9,737,678 B2 | 8/2017 | Formica et al. |
| 2007/0119459 A1 | 5/2007 | Japuntich et al. |
| 2011/0139158 A1* | 6/2011 | Xue ................. A62B 18/10 128/206.15 |
| 2016/0082214 A1 | 3/2016 | Barlow et al. |
| 2016/0184548 A1 | 6/2016 | Wallnewitz et al. |
| 2017/0368289 A1 | 12/2017 | Baiko et al. |
| 2019/0001095 A1* | 1/2019 | Rose ................. A61M 16/0605 |
| 2020/0016356 A1* | 1/2020 | Patel ................. A61M 16/208 |

* cited by examiner

VALVE ARRANGEMENT FOR FULL FACE MASK

CROSS-REFERENCE TO PRIOR APPLICATIONS

This application claims the priority benefit under 35 U.S.C. § 371 of International Patent Application No. PCT/EP2018/056918, filed on Mar. 20, 2018, which claims the priority benefit of U.S. Provisional Patent Application No. 62/477,608, filed on Mar. 28, 2017, the contents of which are herein incorporated by reference.

BACKGROUND OF THE INVENTION

1. Field of the Invention

The present invention relates to patient interface devices. The present invention also relates to valve arrangements for patient interface devices.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

Pressure support systems often include anti-asphyxiation mechanisms built into or located near the patient interface device. One known anti-asphyxiation mechanism involves the use of a valve member such as a flapper component located at or about an opening (i.e., an opening to ambient gas) of the pressure support system. When pressure support therapy is being delivered to the patient, the flapper component is structured to block the opening. However, when pressure support therapy is not being delivered to the patient, such as during a fault condition or when the patient is otherwise wearing the patient interface device but the gas flow generator is not turned on, the flapper component is structured to be moved to an open position to allow the patient to breathe ambient gas. In order to function properly, it is critical that the flapper component be able to move between these two positions (i.e., blocking an opening during pressure support therapy, and not blocking the opening when therapy is not being delivered). A potentially asphyxiating condition could result if a patient were wearing a patient interface device, pressure support therapy was not being delivered, and a flapper component was blocking its opening.

SUMMARY OF THE INVENTION

Accordingly, it is an object of the present invention to provide an improved patient interface device and valve arrangement for the same.

As one aspect of the disclosed concept, a valve arrangement is provided for a patient interface device for use in delivering a flow of breathing gas to an airway of a patient.

The patient interface device includes a frame portion defining a cavity therein which is adapted to receive the flow of breathing gas prior to passing to the airway of the patient. The valve arrangement comprises a valve member having a coupling portion and a blocking portion extending from the coupling portion, the coupling portion being structured to be coupled to the frame portion, the blocking portion being structured to sealingly engage about an aperture which provides a passage between the cavity and an exterior environment, the blocking portion being structured to move between a first position and a second position; and a guard member having a coupling portion and a protecting portion extending from the coupling portion, the coupling portion being structured to be coupled to the frame portion. When the blocking portion of the valve member moves from the first position toward the second position, the blocking portion moves toward the protecting portion of the guard member.

As another aspect of the disclosed concept, a patient interface device for use in delivering a flow of breathing gas to an airway of a patient is provided. The patient interface device comprises a sealing portion adapted to sealingly engage about at least a mouth of the patient; a frame portion supporting the sealing portion and defining a cavity therein which is adapted to receive the flow of breathing gas prior to passing to the airway of the patient; and at least one anti-asphyxia arrangement. The anti-asphyxia arrangement comprises an aperture defined in the frame portion, the aperture being positioned and structured to allow passage of ambient air into the cavity from the surrounding environment, a valve member having a coupling portion and a blocking portion extending from the coupling portion, the coupling portion being coupled to the frame portion, the blocking portion being structured to move between a first position wherein the blocking portion seals about the aperture and prevents the ambient air from passing through the aperture, and a second position wherein at least a portion of the blocking portion is spaced from the aperture, thus allowing ambient air to pass through the cavity into the aperture. The anti-asphyxia arrangement further comprises a guard member having a coupling portion and a protecting portion extending from the coupling portion, the coupling portion being coupled to the frame portion. The protecting portion of the guard member is positioned and structured to be disposed between the blocking portion of the valve member and the mouth of the patient when the sealing portion is sealingly engaged about the at least a mouth of the patient. When the blocking portion of the valve member moves from the first position toward the second position, the blocking portion moves toward the protecting portion of the guard member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly (i.e., one part is positioned in or directly on another part) or indirectly (i.e., through one or more intermediate parts or components), so long as a link occurs. As used herein, "directly coupled" means that two elements are directly in contact with each other.

As used herein, the word "unitary" means a component that is created as a single piece or unit. Under this definition, a component that includes pieces that are created separately and then coupled together as an assembled unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the phrase "sealingly engage" shall mean elements which contact each other in a manner such that a generally air-tight seal is formed therebetween.

As used herein in arrangements in which attractive forces are utilized, "magnetic materials" include materials that are attracted to iron or steel, e.g., a typical magnet, and a material such as iron, steel, or another magnet to which the first material is attracted. It is understood that the purpose of two "magnetic materials" in such arrangements is to have the two materials magnetically attracted to each other. Thus, two non-magnetized materials, e.g. two pieces of normal steel, are not "magnetic materials" in such arrangements.

As used herein, two or more elements which interact in an "attractive manner" are generally drawn toward each other via magnetic forces (e.g., without limitation, two magnets which are arranged having opposing poles (i.e., N-S, S-N) facing each other).

Figure 1:
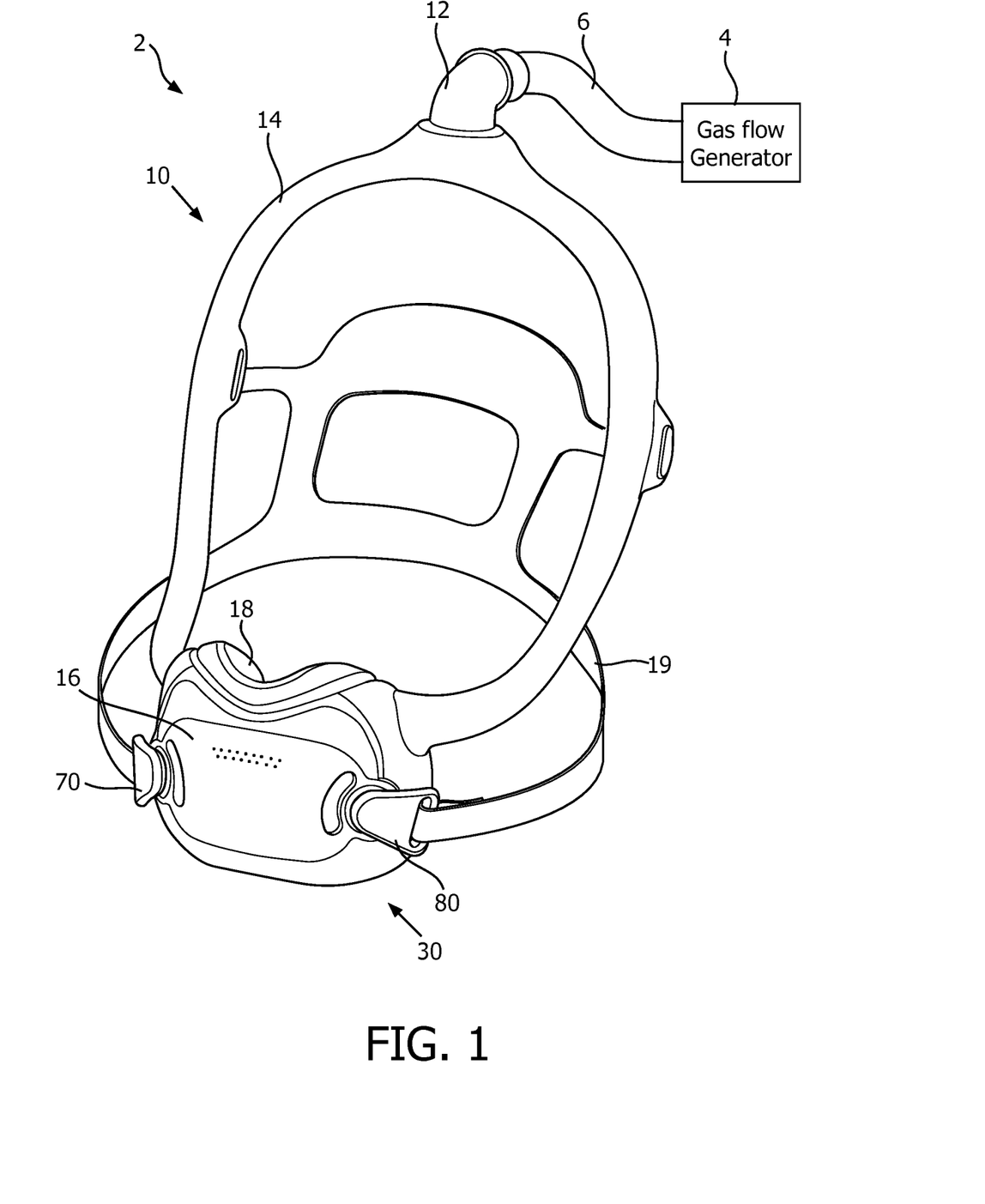
FIG. 1 is a partially simplified isometric view of a pressure support system, in accordance with one non-limiting embodiment of the disclosed concept.

FIG. 1 is a partially simplified view of a pressure support system 2, in accordance with one non-limiting embodiment of the disclosed concept. Pressure support system 2 includes a gas flow generator 4 (shown schematically), a conduit (e.g., without limitation, hose 6, shown schematically) fluidly coupled to gas flow generator 4, and a patient interface device 10. Gas flow generator 4 is structured to generate a flow of breathing gas to be delivered to an airway of a patient. Patient interface device 10 includes an elbow member 12 coupled to hose 6, a conduit 14 coupled to elbow 12, a frame portion 16 coupled to conduit 14, a sealing portion 18 supported by and extending from frame portion 16, a headgear 19 adapted to be secured to the head of the patient, and a number of clip members 70,80 each coupled to headgear 19. In the exemplary embodiment, sealing portion 18 is adapted to sealingly engage about a mouth and a nose of a patient. Additionally, although frame portion 16 and sealing portion 18 are depicted as being separate elements, it is within the scope of the disclosed concept for a suitable alternative patient interface device (not shown) to employ a sealing portion and a frame portion formed as a single unitary element.

Figure 2:
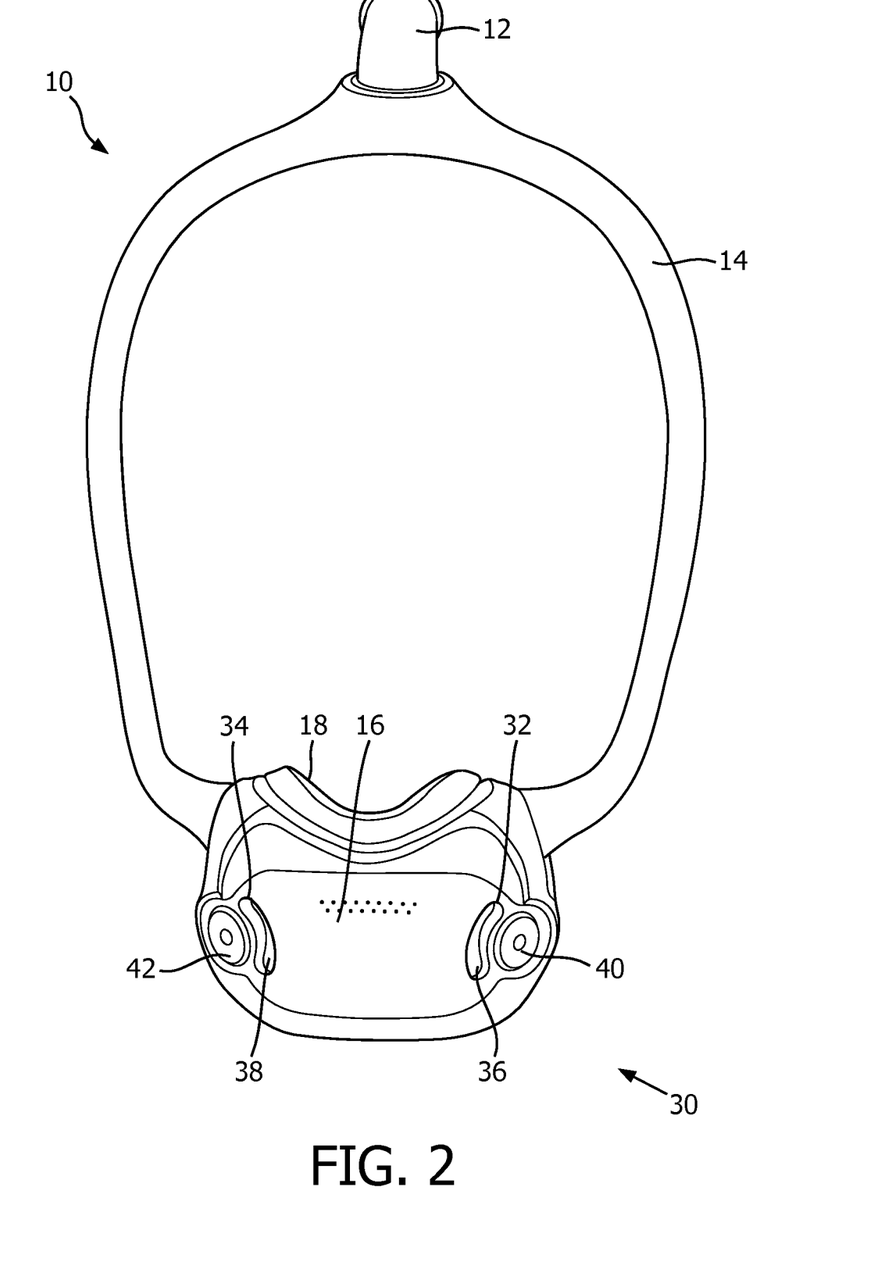
FIG. 2 is a front view of a patient interface device for the pressure support system of FIG. 1, with portions not shown in order to see hidden structures.
Figure 3:
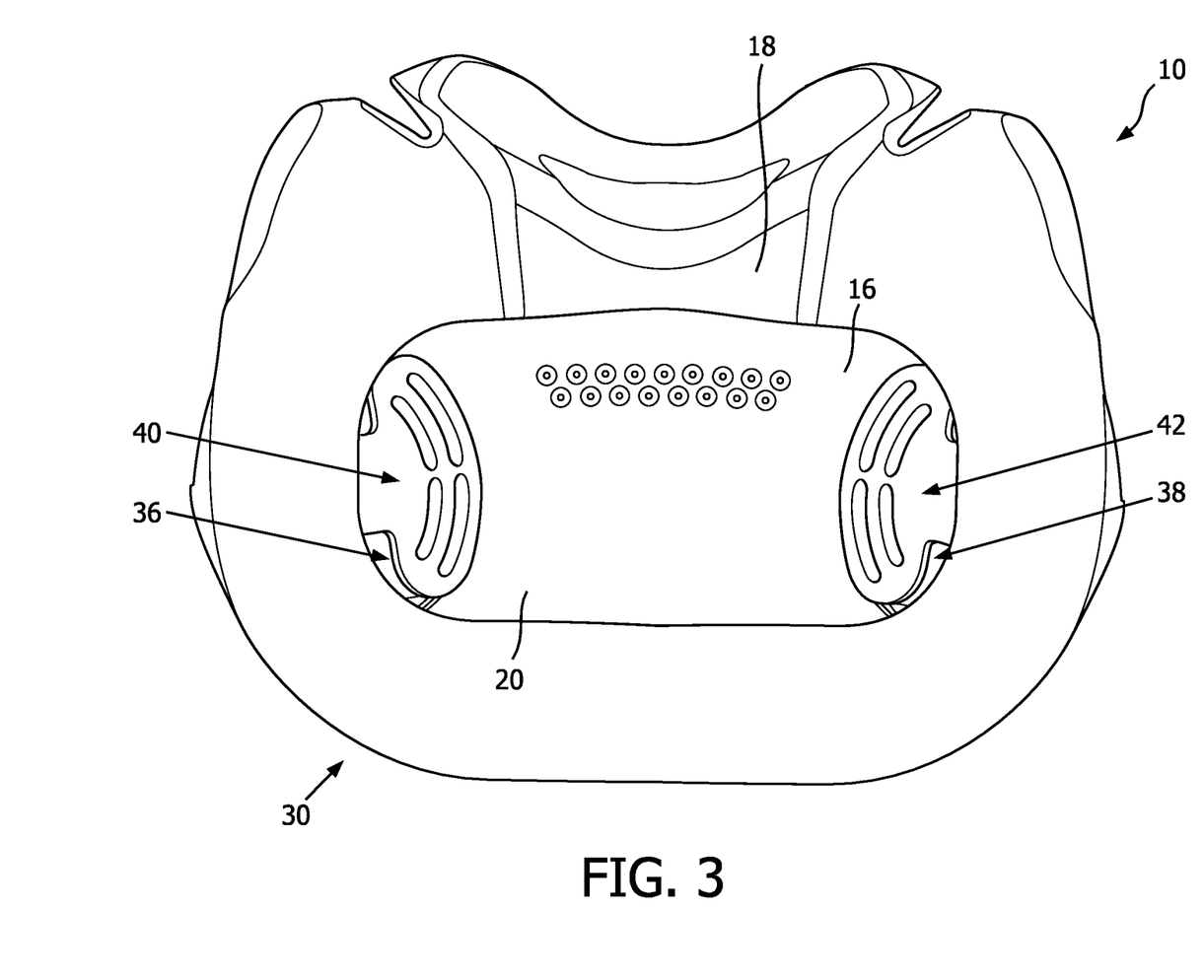
FIG. 3 is a rear view of a portion of the patient interface device of FIG. 2, with additional portions not shown for ease of illustration.

Accordingly, gas flow generator 4 passes the flow of breathing gas through hose 6, elbow 12, and into conduit 14. FIG. 2 shows a front view of a portion of patient interface device 10, and FIG. 3 shows a rear view of a portion of patient interface device 10, each with some parts of patient interface device 10 not shown. Frame portion 16 defines a cavity 20 (shown in FIG. 3) that receives the flow of breathing gas from conduit 14 prior to passing to the airway of the patient.

Figure 4:
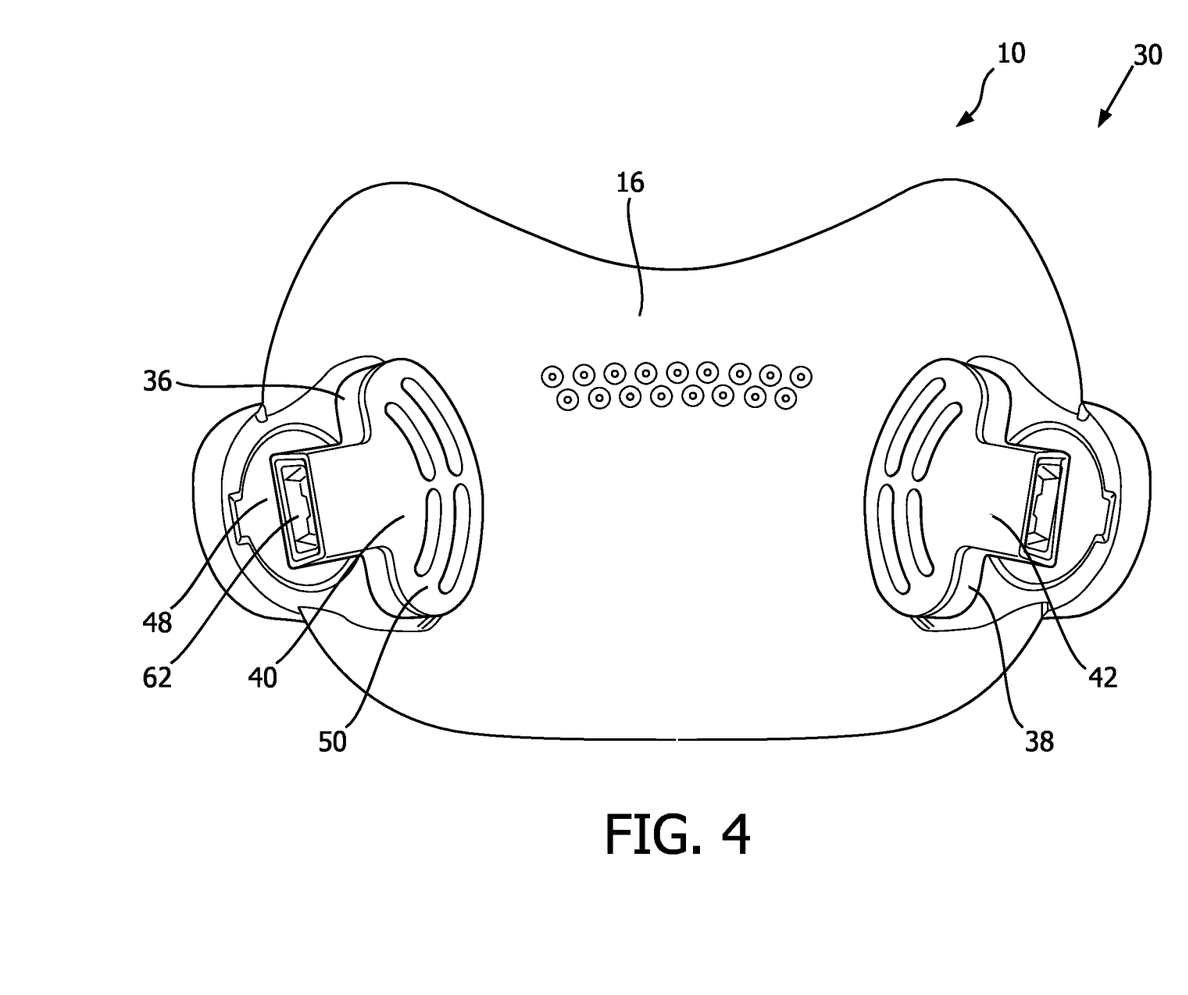
FIG. 4 is another rear view of the patient interface device of FIG. 3, with additional portions not shown in order to see hidden structures.
Figure 6:
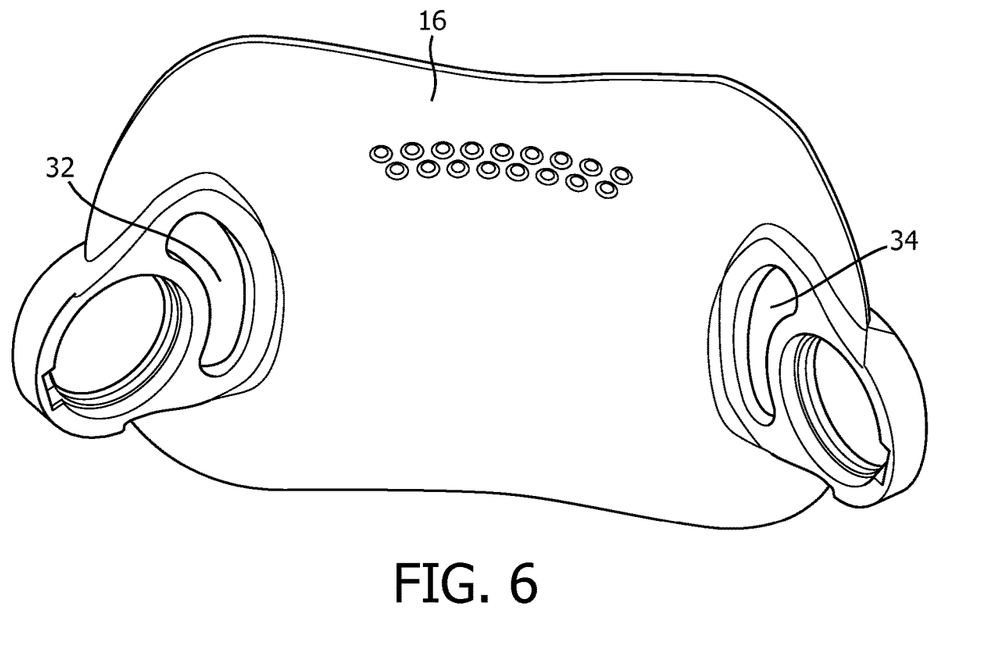
FIG. 6 is a rear isometric view of a portion of a frame portion of the patient interface device of FIG. 4.

FIG. 4 shows another rear view of patient interface device 10, with additional portions of patient interface device 10 not shown in order to see hidden structures. In accordance with the disclosed concept, patient interface device 10 includes a novel anti-asphyxia arrangement 30 for providing protection to the patient against potentially asphyxiating operating conditions. Anti-asphyxia arrangement 30 includes a number of apertures 32,34 (see FIGS. 2 and 6) defined in frame portion 16, a number of valve members 36,38, and a number of guard members 40,42. Apertures 32,34 are positioned and structured to allow passage of ambient air into cavity 20 from the surrounding environment. More specifically, apertures 32,34 provide a safety mechanism by which the patient can breathe ambient air in conditions when pressure support therapy from gas flow generator 4 is not being delivered, such as when gas flow generator 4 (FIG. 1) is turned off during a fault condition. However, valve members 36,38 provide a mechanism by which apertures 32,34 can be sealed when pressure support therapy is being delivered. For ease of illustration and economy of disclosure, only the interaction between aperture 32, valve member 36, and guard member 40 will be discussed in greater detail below. It will, however, be appreciated that aperture 34, valve member 38, and guard member 42 interact in substantially the same manner as aperture 32, valve member 36, and guard member 40, respectively. It will also be appreciated that an alternative patient interface device (not shown) may have any suitable number of apertures/valve members/guard members, without departing from the scope of the disclosed concept.

Figure 5A:
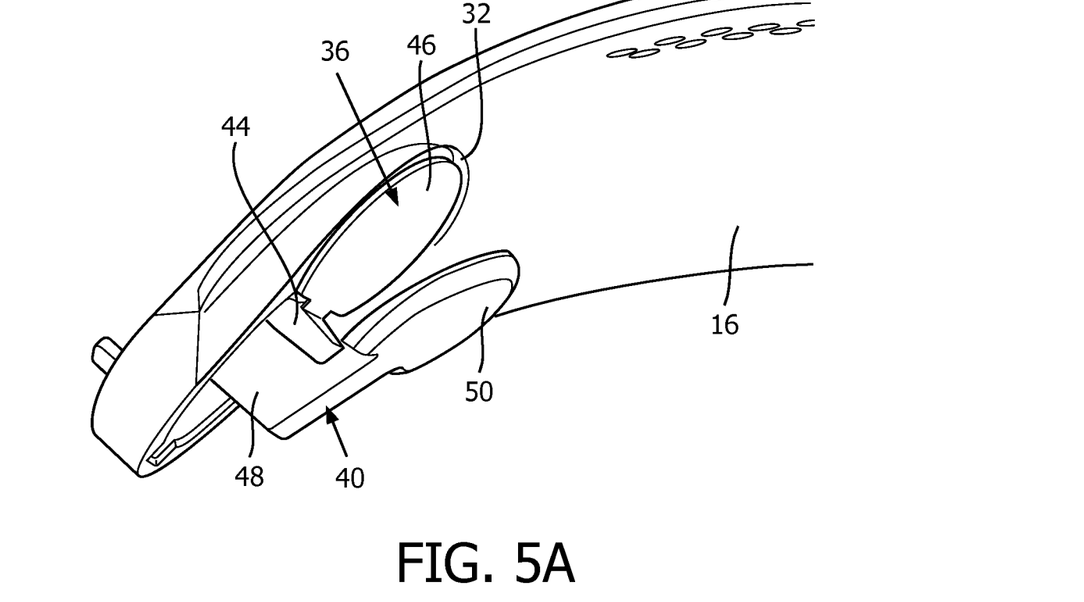
FIG. 5A is an isometric view of a portion of the patient interface device of FIG. 4, shown with a blocking portion of a valve member disposed in a first position.

Referring to FIG. 5A, valve member 36 includes a coupling portion 44 and a generally planar blocking portion 46 extending from coupling portion 44. Guard member 40 includes a coupling portion 48 and a generally planar protecting portion 50 extending from coupling portion 48. In one exemplary embodiment, coupling portion 44 of valve member 36 and coupling portion 48 of guard member 40 are coupled to frame portion 16. Additionally, in the exemplary embodiment, each of valve members 36,38 and guard members 40,42 is a unitary component made from a single piece of material. However, it will be appreciated that a suitable alternative patient interface device (not shown) may employ valve members and/or guard members that are structured differently (e.g., without limitation, that are integral with frame portions rather than being separately coupled thereto). Furthermore, in one example embodiment, valve member 36 is made of a relatively flexible material (e.g., without limitation, silicone) and guard member 40 is made of a relatively rigid material (e.g., without limitation, a thermoplastic material). Accordingly, by virtue of its flexible nature, blocking portion 46 of valve member 36 is advantageously structured to move between positions.

Figure 5B:
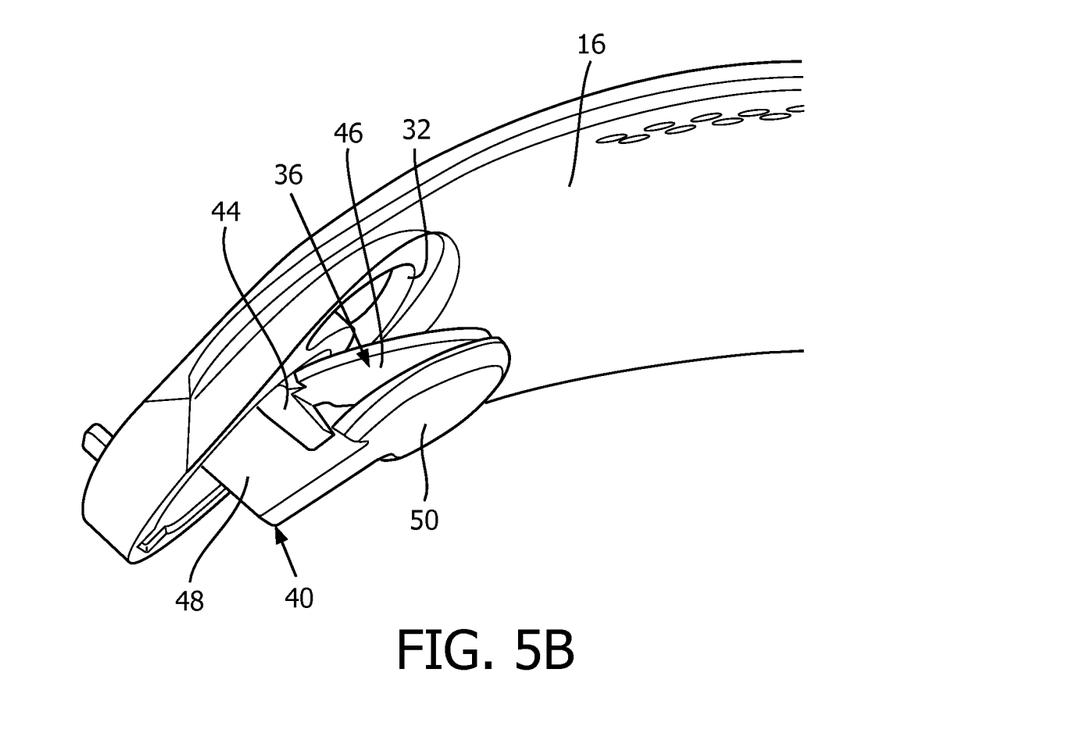
FIG. 5B is another isometric view of the portion of the patient interface device of FIG. 4, shown with the blocking portion of the valve member disposed in a second position.

FIG. 5A shows blocking portion 46 disposed in a first position wherein blocking portion 46 seals about aperture 32 in order to prevent any ambient air from flowing therethrough. Furthermore, when pressure support therapy is being delivered, the pressurized breathing gas causes blocking portion 46 to be maintained in the first position (FIG. 5A). However, if/when pressure support therapy is turned off (e.g., during a potential fault condition of gas flow generator 4 (FIG. 1)), blocking portion 46 is structured to move from the first position (FIG. 5A) to a second position, which is depicted in FIG. 5B. As shown in FIG. 5B, at least a portion of blocking portion 46 is spaced from aperture 32. In one exemplary embodiment, the entire blocking portion 46 is spaced from aperture 32 in the second position. It follows that when blocking portion 46 is in the second position (FIG. 5B), ambient air is allowed to pass through aperture 32 into cavity 20, and thus to the airway of the patient.

It will be appreciated that protecting portion 50 is positioned and structured to be located between blocking portion 46 of valve member 36 and the mouth of the patient when sealing portion 18 (FIGS. 1-3) is sealingly engaged about the mouth and/or the mouth/nose of the patient. As shown in FIG. 5A, when blocking portion 46 is in the first position, blocking portion 46 and protecting portion 50 are generally spaced from and parallel to each other. Additionally, when blocking portion 46 moves from the first position (FIG. 5A) toward the second position (FIG. 5B), blocking portion 46 moves toward protecting portion 50 of guard member 40. Furthermore, when patient interface device 10 is on the face of the patient, protecting portion 50 is positioned between the patient and both aperture 32 and blocking portion 46. Accordingly, it will be appreciated that protecting portion 50 advantageously functions as a barrier between the patient and valve member 36.

More specifically, protecting portion 50, which is relatively rigid, is able to substantially ensure that no portion of the face of the patient will press into blocking portion 46 of valve member 36 and prevent valve member 36 from functioning as intended. As such, patients with certain facial features (e.g., without limitation, relatively large lips and/or facial hair) advantageously have a reliable mechanism to guard against potentially asphyxiating conditions. That is, rather than having the facial features press into valve member 36 and cause blocking portion 46 to seal against aperture 32 when pressure support therapy is not being delivered (i.e., what would be a potentially dangerous asphyxiating condition), protecting portion 50 of guard member 40 significantly increases the likelihood that blocking portion 46 will be able to open and allow ambient air to flow through aperture 32 in such an operating condition. Accordingly, patient interface device 10 advantageously employs anti-asphyxiating features proximate the cushion. This is advantageous to patients who have existing pressure support system components (e.g., without limitation, elbow members) that are devoid of anti-asphyxiation features.

Figure 7A:
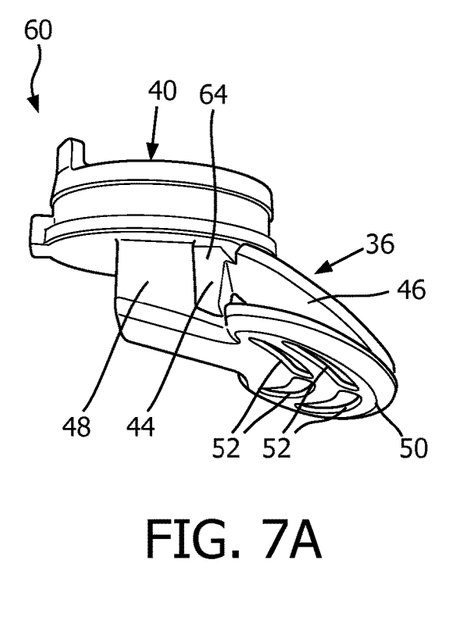
FIGS. 7A and 7B are different views of a valve arrangement for the patient interface device of FIG. 4.
Figure 7B:
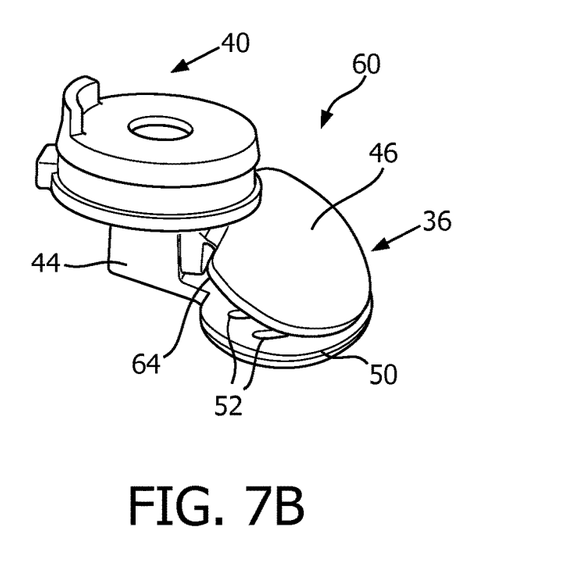

In one exemplary embodiment, coupling portion 44 of valve member 36 is directly coupled to coupling portion 48 of guard member 40. FIGS. 7A and 7B are different views of valve member 36 and guard member 40, which are in the form of a valve arrangement 60. As shown, protecting portion 50 has a number of thru holes (a plurality of thru holes 52 are shown in FIG. 7A and FIG. 7B). Thru holes 52 advantageously allow gas to flow through protecting portion 50 to push blocking portion 46 of valve member 36 towards the first position (FIG. 5A) in order to close aperture 32 in normal operating conditions (i.e., when pressure support therapy is being delivered). It will, however, be appreciated that employing thru holes 52 is one method of ensuring that the flow of gas properly actuates blocking portion 46 of valve member 36. For example and without limitation, it is within the scope of the disclosed concept for a suitable alternative guard member (not shown) to not have through holes, but have a different geometry which is still structured to promote the flow of gas to actuate blocking portion 46 of valve member 36 in all situations.

Figure 8A:
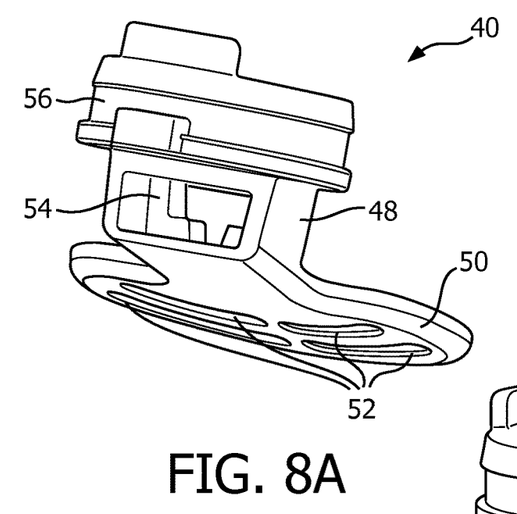
FIGS. 8A and 8B are different views of a guard member for the valve arrangement of FIGS. 7A and 7B.
Figure 8B:
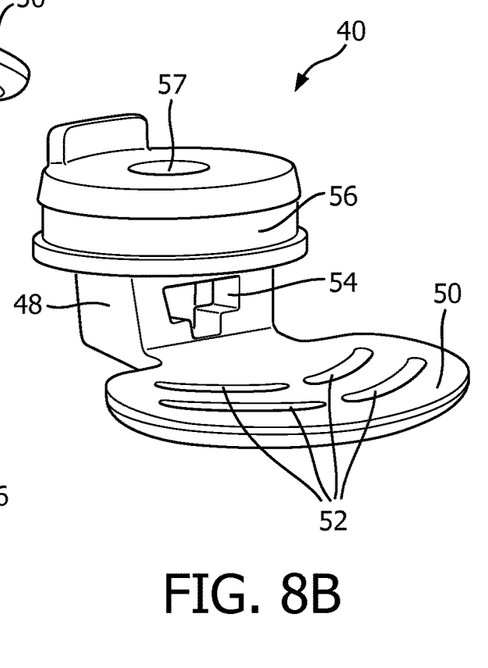
Figure 9A:
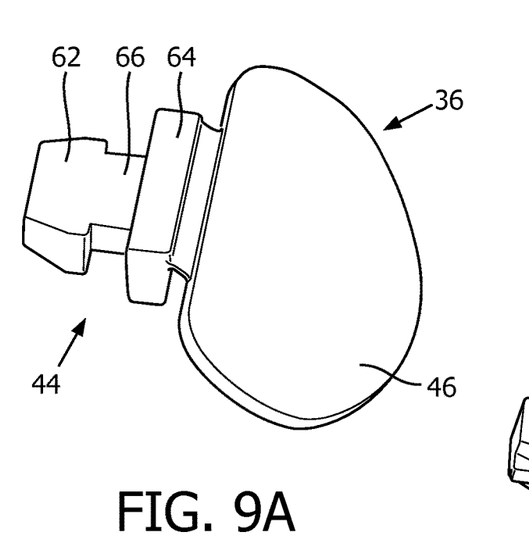
FIGS. 9A and 9B are different views of a valve member for the valve arrangement of FIGS. 7A and 7B.
Figure 9B:
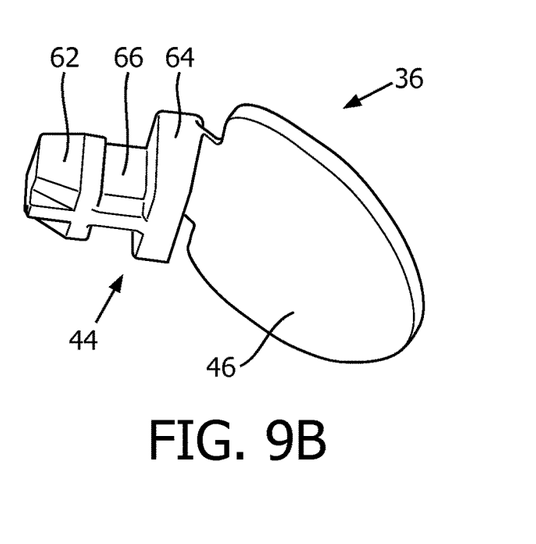

FIG. 8A and FIG. 8B show different views of guard member 40. As shown, coupling portion 48 of guard member 40 has a receiving portion 54 having a thru hole. FIG. 9A and FIG. 9B show different views of valve member 36. As shown, coupling portion 44 of valve member 36 includes a first portion 62, a second portion 64 located opposite first portion 62, and a middle portion 66 between first portion 62 and second portion 64. It will be appreciated that in the exemplary embodiment, middle portion 66 of valve member 36 extends through the thru hole of receiving portion 54 of guard member 40, and first and second portions 62,64 are each structured to engage opposing sides of receiving portion 54 in order to directly couple valve member 36 to guard member 40.

Accordingly, manufacture of valve arrangement 60 (FIG. 7A and FIG. 7B) is relatively simple. More specifically, before installation into patient interface device 10, valve member 36 typically will have a tail (not shown) extending outwardly from and being integral with first portion 62 (FIG. 9A and FIG. 9B). In order to manufacture and/or assemble valve arrangement 60 (FIG. 7A and FIG. 7B), the operator need only insert the tail (not shown) through the thru hole of receiving portion 54 (FIG. 8A and FIG. 8B) of guard member 40, pull until the relatively flexible first portion 62 and second portion 64 are firmly positioned on opposing sides of receiving portion 54, and then trim the tail (not shown).

Referring again to FIG. 8A and FIG. 8B, coupling portion 48 of guard member 40 further includes a body portion 56 extending from receiving portion 54. In the exemplary embodiment, body portion 56 is cylindrical-shaped, and has a relatively narrow middle portion, as compared to its end portions. Accordingly, when valve arrangement 60 is installed in patient interface device 10, body portion 56 extends through and is coupled to frame portion 16. In one exemplary embodiment, because guard member 40 is relatively rigid, body portion 56 is coupled to frame portion 16 by a snap-fit mechanism, thus allowing for relatively simple and reliable assembly.

Figure 10:
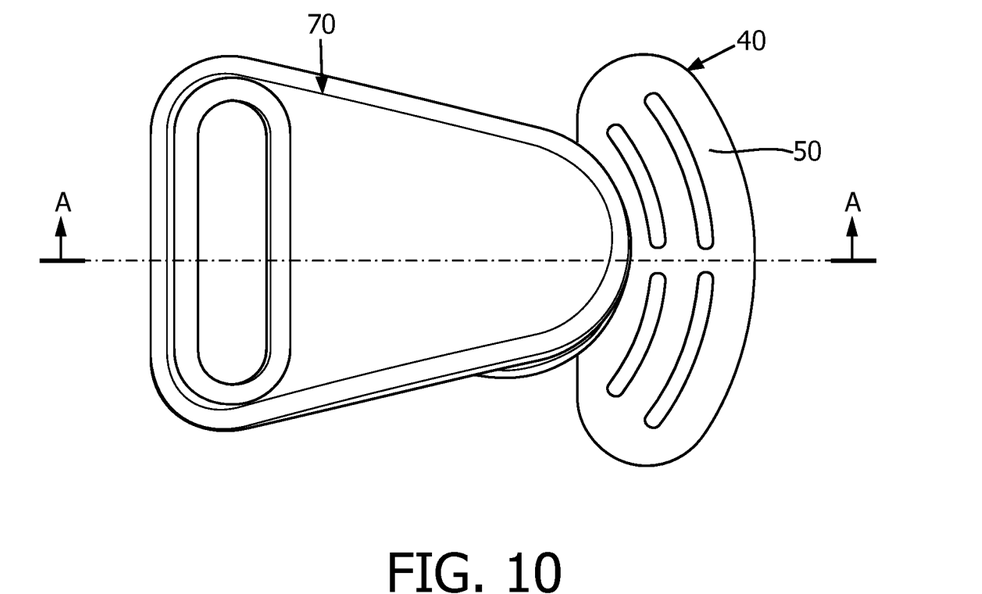
FIG. 10 is a top view of components of the patient interface device of FIG. 4.
Figure 11:
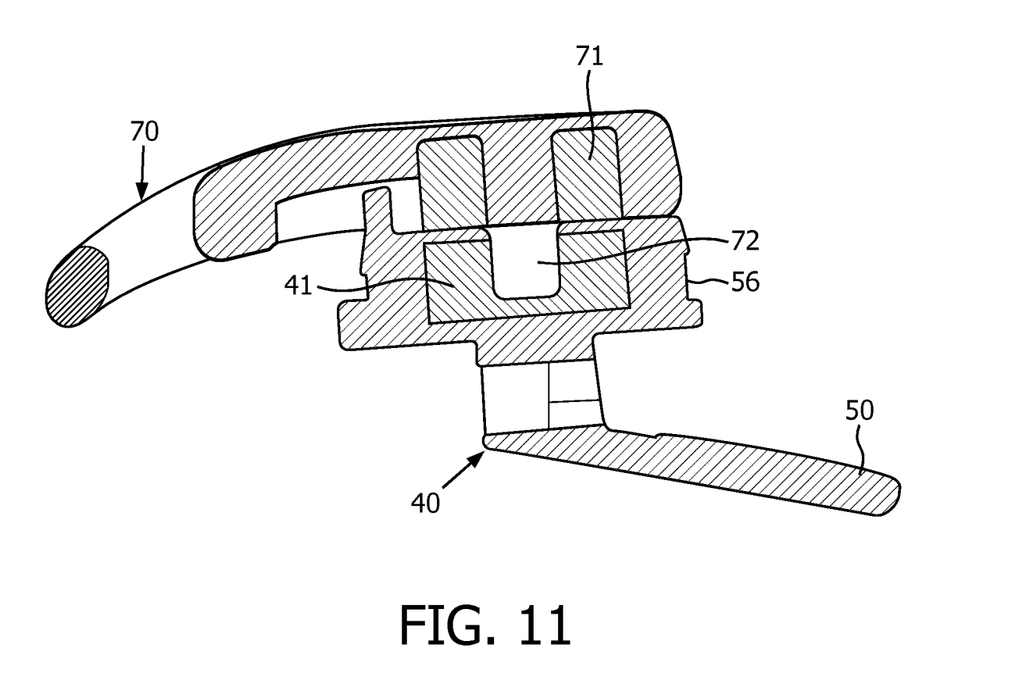
FIG. 11 is a section view of the components of FIG. 10, taken along line A-A of FIG. 10.

FIG. 10 shows a top view of a clip member 70 for use with a strap of a headgear (e.g., headgear 19), and guard member 40, and FIG. 11 shows a section view of the assembly of FIG. 10. As shown in FIG. 11, clip member 70 has a protrusion 72 which extends into body portion 56 of guard member 40. The connection of protrusion 72 and body portion 56 advantageously prevents lateral movement of clip member 70 with respect to guard member 40 when the two are coupled together. However, it will also be appreciated that patient interface device 10 further includes a number of magnetic materials 41,71. As shown in FIG. 11, a magnetic material 41 in the shape of an annulus is provided in or on body portion 56 of guard member 40, and a magnetic material 71 in the shape of an annulus is provided in or on clip member 70. During assembly, magnetic material 41 may be overmolded by guard member 40, and magnetic material 71 may be overmolded by clip member 70. It will be appreciated that magnetic materials 41,71 interact in an attractive manner. Thus, guard member 40 and clip member 70 are reliably coupled to each other by the dual mechanisms of the protrusion 72 and body portion 56 interaction, combined with the magnetic attraction of magnetic materials 41,71. Accordingly, guard member 40 advantageously functions to provide a reliable mechanism to protect against potentially asphyxiating conditions via protecting portion 50, as discussed above, as well as provides a reliable mechanism to couple clip member 70 (i.e., and thus headgear 19, FIG. 1) to patient interface device 10.

Accordingly, it will be appreciated that the disclosed concept provides an improved (e.g., without limitation, safer and easy to manufacture/assemble) patient interface device 10 and valve arrangement 60 therefor.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination. [44] Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for use in delivering a flow of breathing gas to an airway of a patient, the patient interface device comprising:
   (a) a sealing portion adapted to sealingly engage about at least a mouth of the patient;
   (b) a frame portion supporting the sealing portion and defining a cavity therein which is adapted to receive the flow of breathing gas prior to passing to the airway of the patient and having an aperture therein, the aperture being positioned and structured to allow passage of ambient air into the cavity from the surrounding environment; and (c) an anti-asphyxia arrangement comprising:
   (1) a valve member having a coupling portion and a blocking portion extending from the coupling portion, the coupling portion being coupled to the frame portion, the blocking portion being structured to move between:
     (i) a first position wherein the blocking portion seals about the aperture and prevents the ambient air from passing through the aperture, and
     (ii) a second position wherein at least a portion of the blocking portion is spaced from the aperture, thus allowing ambient air to pass through the cavity into the aperture, and
   (2) a guard member having a coupling portion and a protecting portion extending from the coupling portion, the coupling portion being coupled to the frame portion, wherein the protecting portion of the guard member is configured to be positioned and is structured to be disposed between the blocking portion of the valve member and the mouth of the patient when the sealing portion is sealingly engaged about at least the mouth of the patient, and wherein, when the blocking portion of the valve member moves from the first position toward the second position, the blocking portion moves toward the protecting portion of the guard member.

2. The patient interface device according to claim 1, wherein the coupling portion of the guard member is coupled to the frame portion by a snap-fit mechanism.

3. The patient interface device according to claim 1, wherein the coupling portion of the valve member is coupled to the coupling portion of the guard member.

4. The patient interface device according to claim 1, wherein the protecting portion has one or more thru holes.

5. The patient interface device according to claim 1, further comprising a headgear and at least one clip member; and wherein the at least one clip member is coupled to the headgear and the coupling portion of the guard member.

6. The patient interface device according to claim 5, further comprising at least one magnetic material provided in or on the at least one clip member; wherein the anti-asphyxia arrangement further comprises a magnetic material provided in or on the coupling portion of the guard member; and wherein the at least one magnetic material provided in or on the at least one clip member interacts in an attractive manner with the magnetic material provided in or on the coupling portion of the guard member in order to couple the at least one clip member to the coupling portion of the guard member.

7. The patient interface device according to claim 1, wherein the coupling portion of the guard member further has a body portion extending through and being coupled to the frame portion.

* * * * *